(12) United States Patent
Brent et al.

(10) Patent No.: US 10,467,534 B1
(45) Date of Patent: Nov. 5, 2019

(54) AUGMENTED REALITY PROCEDURAL SYSTEM

(71) Applicant: Roger Brent, Seattle, WA (US)

(72) Inventors: Roger Brent, Seattle, WA (US); James Ashley, Lilburn, GA (US)

( * ) Notice: Subject to any disclaimer, the term of this patent is extended or adjusted under 35 U.S.C. 154(b) by 489 days.

(21) Appl. No.: 15/374,971

(22) Filed: Dec. 9, 2016

Related U.S. Application Data

(60) Provisional application No. 62/265,227, filed on Dec. 9, 2015.

(51) Int. Cl.
*G06N 5/02* (2006.01)
*G06K 9/00* (2006.01)
*G06K 9/46* (2006.01)
*G06T 7/269* (2017.01)
*G06F 16/903* (2019.01)

(52) U.S. Cl.
CPC ....... *G06N 5/022* (2013.01); *G06F 16/90335* (2019.01); *G06K 9/00671* (2013.01); *G06K 9/4609* (2013.01); *G06T 7/269* (2017.01)

(58) Field of Classification Search
CPC ... G06N 5/022; G06T 7/269; G06F 16/90335; G06K 9/00671; G06K 9/4609
See application file for complete search history.

(56) References Cited

U.S. PATENT DOCUMENTS 7,477,993 B2 * 1/2009 Sunshine ............... B82Y 15/00
422/82.01
9,418,416 B2 * 8/2016 Milne ................ G01N 21/9027

OTHER PUBLICATIONS

Kloss et. al, "LIGGGHTS and CFDEM coupling—Modelling of macroscopic particle processes based on LAMMPS technology", 2013 (Year: 2013).*

* cited by examiner

*Primary Examiner* — Scott A. Waldron
*Assistant Examiner* — Selene A. Haedi
(74) *Attorney, Agent, or Firm* — Rowan TELS LLC

(57) ABSTRACT

A method of identifying substances in a material handling work environment that analyzes sensor input from the environment with an image processor to extract features of the substance using optical flow and object recognition, and operates a vector modeler and a particle modeler to generate multiple predictions about particle movement within the substance based on existing data models for physical properties to generate multiple predictions of physical properties of the substance.

7 Claims, 13 Drawing Sheets

AUGMENTED REALITY PROCEDURAL SYSTEM

CROSS-REFERENCE TO RELATED APPLICATIONS

This application claims priority and benefit under 35 U.S.C. 119 U.S. application Ser. No. 62/265,227, filed on Dec. 9, 2015, entitled "AUGMENTED REALITY PHYSICS ENGINE", which is incorporated herein by reference in its entirety.

BACKGROUND

Material handling generally, and in laboratories specifically, can benefit from greater uniformity, consistency, reliability, reproducibility, quality, and integrity. Laboratory protocols or laboratory notebooks may improve some of these issues, but reference a protocol manual or lab notebook for an experimental protocol or procedure can be time consuming and tedious. In addition, some protocols and procedures may require measurement value and results to be reported after each measurement or at intervals that may overlap with the preparation of a subsequent step of the action set.

Identification and material mixing is a common part of everyday life, and even more so in the life of a scientist. Determining the outcomes of various interactions of known and unknown substances is a challenging problem to overcome. Further, the physical properties calculated by current physics engines are generally restricted to physics, and fail to take into account the effect of additional science fields on materials. Controlling computer interfaces and peripheral machines based on these interactions creates another level of complexity.

The following references provide background on the material disclosed herein:

Eppela, S. and Kachman, T. (2014) Computer vision-based recognition of liquid surfaces and phase boundaries in transparent vessels, with emphasis on chemistry applications. arXiv preprint arXiv: 1404.7174

Fraczek J, Zlobecki, A., and Zemanek, J. (2007) Assessment of angle of repose of granular plant material using computer image analysis. Journal of Food Engineering 83, 17-22

OpenSim. (2016) Referencing OpenSim Arm26 model and OpenSim itself download 18 Nov. 2016.

RecFusion (2016). Software by imFusion GmbH, Munich, ImFusion GmbH, Agnes-Pockels-Bogen 1 80992 München, Germany. Downloaded 18 Nov. 2016.

Vassiliou, E., Giunto, G. F., Schaefer, W. R., Kahn, B. R. (1994). Slag viscosity detection through image analysis of dripping slag within rotary incineration kilns. U.S. Pat. No. 5,301,621.

BRIEF SUMMARY

Disclosed herein are augmented reality (AR) systems and procedures to enable AR device such as the Microsoft® Hololens® to factilitate material handling activities. The systems and procedures may be applied to chemistry, biology, construction, manufacturing, cooking, and many other activities that involve material handling and which benefit from being reproducable and teachable.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
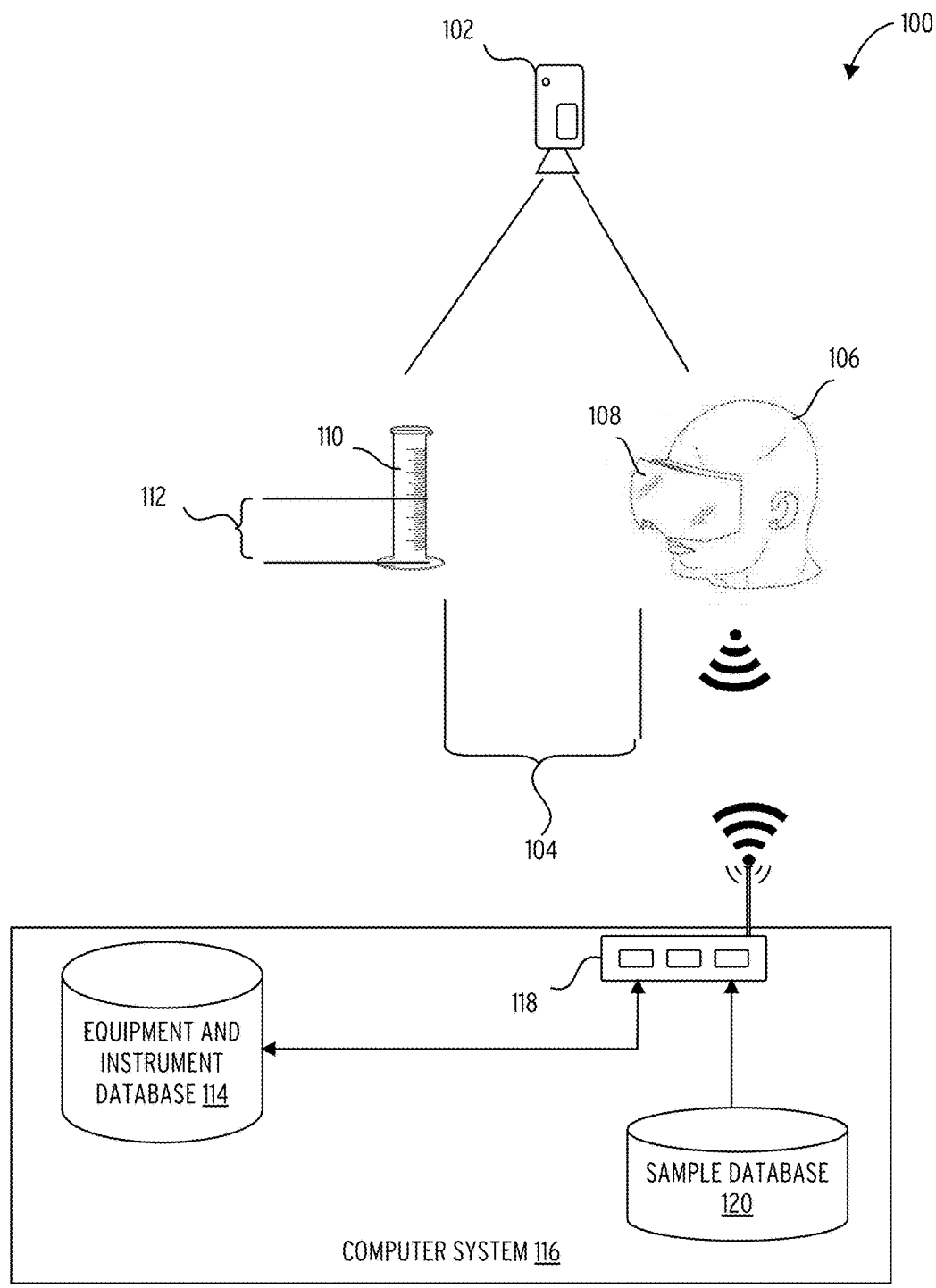
FIG. 1 illustrates an aspect of an augmented reality measurement system 100 including a computer system 116 in accordance with one embodiment.

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

The terminology used herein has its conventional meaning in the relevant arts except where defined below:

"Augmented reality" in this context refers to is a live direct or indirect view of a physical, real-world environment whose elements are augmented (or supplemented) by computer-generated sensory input such as sound, video, graphics or GPS data, in real time, to enhance a user's current perception of reality. Augmented reality herein also refers to purely virtual environments influenced by objects or actions in the physical world (i.e., "virtual reality").

"Augmented virtuality" in this context refers to the dynamic integration of physical (real) world objects or actions to interact with a virtual environment.

"Comparative Physical Modeling" in this context refers to a logical component that identifies similarities in the computational model of a detected object's physical attributes with existing models of known materials under the same measurement conditions.

"Environmental Signal" in this context refers to a complex of sensory signals originating from a plurality of sensors measuring physical attributes of a protocol environment.

"Graphical Overlay" in this context refers to a transparent visual layer on a display partially obscured by graphical objects.

"Mixed Reality" in this context refers to the merging of real and virtual world objects and interactions to produce new environments and visualisations where physical and digital objects co-exist and interact in real time.

"Particle modeler" in this context refers to logic to perform particle behavior modeling. Open source particle modeling logic includes LIGGGHTS® and E-Sys Particle. Particle modelers build a computational model of a given particle system based on observed attributes of the particle system and known (previously stored) attributes of substances.

"Quantifying Features" in this context refers to structures or regions of a laboratory instrument visually inspected to obtain measurements or values.

"Spatiotemporal Movement Analysis" in this context refers to a logic component that derives physical attributes to generate a computational model for a detected object in the protocol environment.

"User Space" in this context refers to a voided region occupiable by a user operating an augmented reality device.

Vector modeler" in this context refers to any logic to model 2D or 3D processes or motion using vectors. Conventional systems providing vector modeling logic include QGIS open source vector modeler library, and the Live2D® modeler from Live2D Corp. Vector modelers construct vectors for the mechanics of motion for an object or particle. This may involve reading and calculating force, velocity, acceleration and other aspects of kinematics, statics and dynamics dealing with the motion of objects.

"Visual display" in this context refers to a display of an augmented reality device that shows a graphical overlay. The visual display may additionally include a representative video layer of the graphical environment. Alternatively, the visual display may be transparent in construction.

"Action multiplexer" in this context refers to a logic component that selects one of several possible analog or digital input signals to initiate an action on a machine by forwarding the selected action input to an output terminal.

"Predictive model" in this context refers to known and observed attributes of substances which are combined to build a data model which enables predictions about future interaction based on the combined attributes of the component substances.

"Sensor" in this context refers to a device or composition of matter that responds to a physical stimulus (as heat, light, sound, pressure, magnetism, or a particular motion) and transmits a resulting impulse (as for measurement or operating a control).

"Associator" in this context refers to a correlator (see the definition for Correlator).

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Classifier" in this context refers to a specific type of correlator/associator logic that associates one or more inputs with a category, class, or other group sharing one or more common characteristics. An example of a classifier that may commonly be implemented in programmable hardware is a packet classifier used in network switches, firewalls, and routers (e.g., packet classifiers utilizing Ternary Content Addressable Memories). An example software or firmware classifier is: if (input1.value<12.5) input1.group=group1; else if (input1.value>=12.5 and input1.value<98.1) input1.group=group2; else input1.group=group3; Other examples of classifiers will be readily apparent to those of skill in the art, without undo experimentation.

"Combiner" in this context refers to a logic element that combines two or more inputs into fewer (often a single) output. Example hardware combiners are arithmetic units (adders, multipliers, etc.), time-division multiplexers, and analog or digital modulators (these may also be implemented is software or firmware). Another type of combiner builds an association table or structure (e.g., a data structure instance having members set to the input values) in memory for its inputs. For example: val1, val2, val3→combiner logic→{val1, val2, val3} set.val1=val1; set.val2=val2; set.val3=val3; Other examples of combiners will be evident to those of skill in the art without undo experimentation.

"Comparator" in this context refers to a logic element that compares two or more inputs to produce one or more outputs that reflects similarity or difference of the inputs. An example of a hardware comparator is an operational amplifier that outputs a signal indicating whether one input is greater, less than, or about equal to the other. An example software or firmware comparator is: if (input1==input2) output=val1; else if (input1>input2) output=val2; else output=val3; Many other examples of comparators will be evident to those of skill in the art, without undo experimentation.

"Correlator" in this context refers to a logic element that identifies a configured association between its inputs. One examples of a correlator is a lookup table (LUT) configured in software or firmware. Correlators may be implemented as relational databases. An example LUT correlator is: |low_alarm_condition |low_threshold_value|0 ||safe_condition |safe_lower_bound |safe_upper_bound |high_alarm_condition|high_threshold_value|0| Generally, a correlator receives two or more inputs and produces an output indicative of a mutual relationship or connection between the inputs. Examples of correlators that do not use LUTs include any of a broad class of statistical correlators that identify dependence between input variables, often the extent to which two input variables have a linear relationship with each other. One commonly used statistical correlator is one that computes Pearson's product-moment coefficient for two input variables (e.g., two digital or analog input signals). Other well-known correlators compute a distance correlation, Spearman's rank correlation, a randomized dependence correlation, and Kendall's rank correlation. Many other examples of correlators will be evident to those of skill in the art, without undo experimentation.

"Firmware" in this context refers to software logic embodied as processor-executable instructions stored in read-only memories or media.

"Hardware" in this context refers to logic embodied as analog or digital circuitry.

"incrementer" in this context refers to logic to advance (increase or decrease) a counting or index value by a fixed or predictably variable amount. Examples of hardware incrementers include adder arithmetic circuits and counter circuits. An example of a software incrementer is: x=x+incrementValue. Incrementers may be used as counters, or as logic to advance a referencial or associative index in a memory data structure.

"Logic" in this context refers to machine memory circuits, non transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Parser" in this context refers to logic that divides an amalgamated input sequence or structure into multiple individual elements. Example hardware parsers are packet header parsers in network routers and switches. An example software or firmware parser is: aFields=split("val1, val2, val3", ","); Another example of a software or firmware parser is: readFromSensor gpsCoordinate; x_pos=gpsCoordinate.x; y_pos=gpsCoordinate.y; z_pos=gpsCoordinate.z; Other examples of parsers will be readily apparent to those of skill in the art, without undo experimentation.

"Programmable device" in this context refers to an integrated circuit designed to be configured and/or reconfigured after manufacturing. The term "programmable processor" is another name for a programmable device herein. Programmable devices may include programmable processors, such as field programmable gate arrays (FPGAs), configurable hardware logic (CHL), and/or any other type programmable devices. Configuration of the programmable device is generally specified using a computer code or data such as a hardware description language (HDL), such as for example Verilog, VHDL, or the like. A programmable device may include an array of programmable logic blocks and a hierarchy of reconfigurable interconnects that allow the programmable logic blocks to be coupled to each other according to the descriptions in the HDL code. Each of the programmable logic blocks may be configured to perform complex combinational functions, or merely simple logic gates, such as AND, and XOR logic blocks. In most FPGAs, logic blocks also include memory elements, which may be simple latches, flip-flops, hereinafter also referred to as "flops," or more complex blocks of memory. Depending on the length of the interconnections between different logic blocks, signals may arrive at input terminals of the logic blocks at different times.

"Selector" in this context refers to a logic element that selects one of two or more inputs to its output as determined by one or more selection controls. Examples of hardware selectors are multiplexers and demultiplexers. An example software or firmware selector is: if (selection_control==true) output=input1; else output=input2; Many other examples of selectors will be evident to those of skill in the art, without undo experimentation.

"Sequencer" in this context refers to logic to generate an ordered list of outputs from either an unordered or partially ordered set of inputs, or from a starting input and rules to generate next inputs. One attribute of a sequencer is that the outputs are done sequentially, meaning one after the other in time. An example of a hardware sequencer is a multiplexer with a counter driving its selection input. An example of a software or firmware sequencer is: out=val++; Other examples of hardware and software or firmware sequencers will now be readily apparent to those of skill in the relevant arts.

"Software" in this context refers to logic implemented as processor-executable instructions in a machine memory (e.g. read/write volatile or nonvolatile memory or media).

"Switch" in this context refers to logic to select one or more inputs to one or more outputs under control of one or more selection signals. Examples of hardware switches are mechanical electrical switches for switching power to circuits, devices (e.g., lighting), or motors. Other examples of hardware switches are solid-state switches such as transistors. An example of a hardware or firmware switch is: if (selection==true) output=input; else output=0; A somewhat more complicated software/firmware switch is: if (selection1==true and selection2==true) output=input1; else if (selection1==true and selection2==false) output=input2; else if (selection1==false and selection2==true) output=input3; else output=noOp; Switches operate similarly to selectors in many ways (see the definition of Selector), except in some cases switches may select all inputs to the output(s) not select among inputs. Other examples of switches will be readily apparent to those having skill in the art, without undo experimentation.

An augmented reality device is provided to assist users in performing new or unfamiliar experimental techniques, identify materials and products utilized in a documented action set and within a work environment, identify equipment and instruments needed in the documented action set and within the work environment, assist in performing single person (autonomous) work, collaborate with other workers, and record data and observations in an electronic notebook.

A method of guiding and documenting procedural actions of an action set may be provided with an augmented reality device, operatively disposed to a user space, comprising a processor, memory, a plurality of external transducers, a plurality of internal transducers, and a visual display, and provided with a graphical overlay superimposed on an ocular field of view represented on the visual display.

An environmental signal, captured through a plurality of external transducers, may be transformed into an image map including detected objects. Equipment and instruments may be recognized from the detected objects through comparative analysis of visual characteristics of the detected objects with known visual characteristics in an equipment and instrument database.

Materials and products may be identified from the detected objects through spatiotemporal movement analysis, comparative physical modeling, and referencing a materials database. The detected objects may be synchronized to the graphical overlay to coincidently align the detected objects of the image map with the environmental objects of the interaction environment to the ocular field of view through operations of the processor controlled by overlay synchronization logic.

Objects of interest within the image map are recognized by transforming an ocular movement tracking signal, captured by a plurality of internal transducers, into an ocular line of sight directed towards an environmental object in the interaction environment, with a corresponding detected object in the image map. Procedural actions are recognized through contextual visual behavior recognition by tracking spatiotemporal movement of the materials and products relative to the equipment and instruments in the series of sequential image maps, and correlating to documented procedural actions in an action set database as controlled by behavior identification logic.

The augmented reality measurement system may provide active guidance for performing lab procedures, including visual indicators identifying a next action to take as an overlay on material or equipment from the ocular field of view displayed on the image map. The augmented reality measurement system may also identify and visually indicate procedural errors when the user's actions do not comport with a next action to take.

Quantifiable data may be captured by quantifying features of the equipment and instruments through contextual feature analysis, and by correlating the procedural action and the ocular line of sight to the quantifying features of the equipment and instruments in the series of sequential image maps, and visualizing a guided interaction overlay as the graphical overlay in response to an action set selection input of a documented action set from the action set database. The guided interaction overlay may include directional indicators such as arrows, dots, lines, and text (for example) indicating equipment or materials with which to interact, operating or material handling instructions, and/or next actions to take.

An action set outline may be visualized detailing the documented procedural actions of the documented action set through the guided interaction overlay. A list of materials and a list of equipment and instruments utilized in the documented action set may also be visualized through the guided interaction overlay. A graphical identifier aligned to the detected objects may be displayed in the image map corresponding to materials, equipment, and instruments in the interaction environment through the guided interaction overlay. One or more advisement notifications may be displayed through the guided interaction overlay in response to detecting an advisement and precaution alert associated with particular documented procedural actions.

In some embodiments, the augmented reality device includes a user interface to receive vocalized inputs. The vocalized inputs may be equipment and instrument identifiers, material and product identifiers, interaction environment identifiers, or an action set modification narrative.

In the aforementioned embodiment, equipment and instrument identifiers and material and product identifiers may be recognized from the vocalized input as controlled by speech recognition logic. The equipment and instrument identifiers and the material and product identifiers may be assigned to particular objects of interest as controlled by user-object identification logic. Analysis metrics for the behavior identification logic and the object recognition logic may be adjusted as controlled by environment-dependent identification logic. An action set modification narrative may be recognized, and in response a modified action set outline may be stored as an interaction entry in an action log allocation of memory as controlled by the action set documentation logic.

Capturing the quantifiable data may include identifying character values in the quantifying features of the equipment and instruments through operations of the processor under control of optical character recognition logic, and storing the character values, equipment and instrument identifiers, material and product identifiers and spatiotemporal identifiers as an interaction entry in an action log allocation of memory as controlled by action set documentation logic.

The quantifiable data, within the interaction entries stored in the action log allocation of memory, may be accessible through a graphical user interface. The graphical user interface may display the quantifiable data mapped to the procedural steps as well as any modified action set outline that occurred during the execution of the action set.

A user may establish particular attributes for the interaction environment and for objects within the interaction environment through a user interface. The user interface may accept direct inputs such as text input and vocalized input to establish identification of a particular interaction environment or a particular object. Through the identification of the particular interaction environment and/or the particular object, the system retrieves established attributes and prioritizes results from the materials database, the equipment and instrument database, and the action set database based on one or more of previous interactions within the particular interaction environment, particular object, previous interactions in protocol environments with similar attributes to the particular interaction environment, or objects with similar attributes to the particular interaction environment. In one example, the user interface may accept textual input identifying an external network database or website detailing attributes of a particular object or particular procedures of an action set.

The augmented reality device is typically communicably coupled to a networked repository that may include the materials database, the equipment and instrument database, and the action set database. The augmented reality device may transmit the environmental signal to a distribution server for distribution to collaborators. The recognition of the materials and products within the series of sequential image maps may be performed as an asynchronous process performed by the processor under control of a subroutine of the object recognition logic.

A plurality of internal transducers (internal to the augmented reality device) may be used to collect a plurality of biometric/physiological readings from a user within the user space. The bio-metric readings may include, but are not limited to, heart rate data, motion data, respiratory data, temperature data, cardiovascular data, and electrophysiological data.

The augmented reality device may be autonomous with on-board autonomous operational logic and data repositories, but is more likely operated using a combination of onboard and external logic and data repositories. Moreover, the augmented reality device may communicate with other researchers and devices worn by and carried by them. The augmented reality device may respond to input and requests from the researcher via cues generated verbally, sub-vocally, by eye movements and other gestures, by head movements, by specific body movement, by learned unconscious body movements, by learned autonomic cues, and combinations of these. These inputs may be received directly or relayed from other devices (e.g. from accelerometers or other sensors on smartphones or smartwatches) on the person of the user or remote from the user (e.g. cameras).

The device may also accept input that requires interactive communication between device and user, in which the user, for example, responds to a request that they mechanically manipulate a container holding some material, from which data the interactive interfaced augmented reality measurement system makes inferences about the material's mass and density. The user may be taught the identities of objects and materials and given additional didactic or useful information about objects in the user's visual field. The interfaced augmented reality measurement system may recognize, identify, and tag laboratory objects in the user's field of view. On request from the user, the augmented reality device may provide additional information (e.g. who the object belongs to, manufacturer of object, vendor, the last time object is known to have been touched or moved). The augmented reality device may request additional input from the user such as information about mass and density of samples inferred from imaging the user hefting a container including the sample.

The user may be taught to perform specific experimental techniques, often, by interaction with online information including information resident in laboratory protocols. In this aspect, the augmented reality measurement system responds to input from the user by identifying specific objects that are the objects of the user's intended manipulation. For example, a user may indicate using voice cues that they want to streak out a bacterial culture onto an agar dish to isolate single colonies. The interactive interface augmented reality device asks the user to examine the lab space, and locate a test tube containing a bacterial culture, a Bunsen burner, a wire loop, and a petri dish with sterile agar. The augmented reality device may show the user text, images and/or video of the procedure, and offer voice, text, or image guidance to the next steps. The user may focus visual attention on some aspect of the procedure at any point. The device may offer the user input as they perform an action on the focused aspect. For example, should the visual image of the procedure deviate from the image the augmented reality device associates with correct performance of the procedure, the augmented reality device may inform the user of the discrepancy. Similarly, the user may stop moving at some point and request comparison with images or video (photographic or animation representation) of the idealized procedure.

The user may be aided by the augmented reality device while they function autonomously in a research lab (i.e. carry out research). The augmented reality measurement system may recognize and accept input on objects in the visual field, for example as described above. The augmented reality device may interact with the user to increase the user's knowledge of expected behaviors that arise while carrying out experiments. The augmented reality measurement system may have or may interface with an Augmented/Mixed Reality Physics Model (AMRPM, as an Augmented/Mixed Reality Laboratory Physics Model, AMRLPM) executing logic (called an Augmented/Mixed Reality Physics Engine, AMRPE, as an Augmented/Mixed Reality Laboratory Physics Engine, AMRLPE) that embodies expectations about behavior of objects, equipment, and substances. Examples include the transfer of heat to liquids in a flask with a stir bar perched on a hotplate, the rate at which different solid compounds dissolve in aqueous buffers, the rate at which different hyrogscopic powdered solids might take on moisture from the air, estimated volumes and masses of solids and liquids from visual data or prompted hefts, the behaviors of liquids and bubbles in tubing and microfluidic devices, etc. The augmented reality measurement system may enable the investigator to compare these expected behaviors to what they are experiencing. The AMRLPM may also aid in training and following procedures as described previously.

The augmented reality measurement system may aid the recording and interpretation of observations. For example, the user may be examining a field of view such as colonies on a bacterial plate, or Arabdopsis plants in a pot. The augmented reality measurement system may identify the visualized objects, recording their number, sizes, and other relevant visual data. The system may then count, catalog and record different categories of objects in the visual field. The system may display this information to the user for their approval. The user may, by interaction with the device, train the interface in more accurate identification, and/or identification that is more consonant with the criteria articulated by the researcher or taught by the researcher, to the AI. This information may be communicated to a research group, via social media, to an archive, etc. The system submit data recorded for research and training via interaction with a human teacher, or for crowd sourced evaluation via entities such as Stack Exchange.

A user of the augmented reality measurement system may work collaboratively with students and researchers, to conduct training or research. The system may enable all of the above uses and collaborative workers may be able to exchange fields of view containing viewed objects and other entities in field of view, may designate objects of common interest, may request input about the field of view and the objects in it, and may participate in other activities, for example interacting to generate consensus determinations about data gathered and recorded.

Referring to FIG. 1, an augmented reality measurement system 100 includes a camera 102, a human operator 106 outfitted with augmented reality headset 108, and a container 110 holding a liquid. The augmented reality measurement system 100 may be used to measure characteristics of a liquid sample in the container 110.

The container 110 is separated from the human operator 106 by a sample distance 104. Within the container 110, the liquid has discernable liquid boundaries 112. The container 110 may be a known type, for example a flask or graduated cylinder, of known volume, for example, a two liter Erlenmeyer flask of standard geometry.

U.S. Pat. No. 5,301,621, by Vassiliou et al. discloses image analysis techniques for measurement of properties of drippings and is incorporated herein by reference in its entirety.

Figure 2:
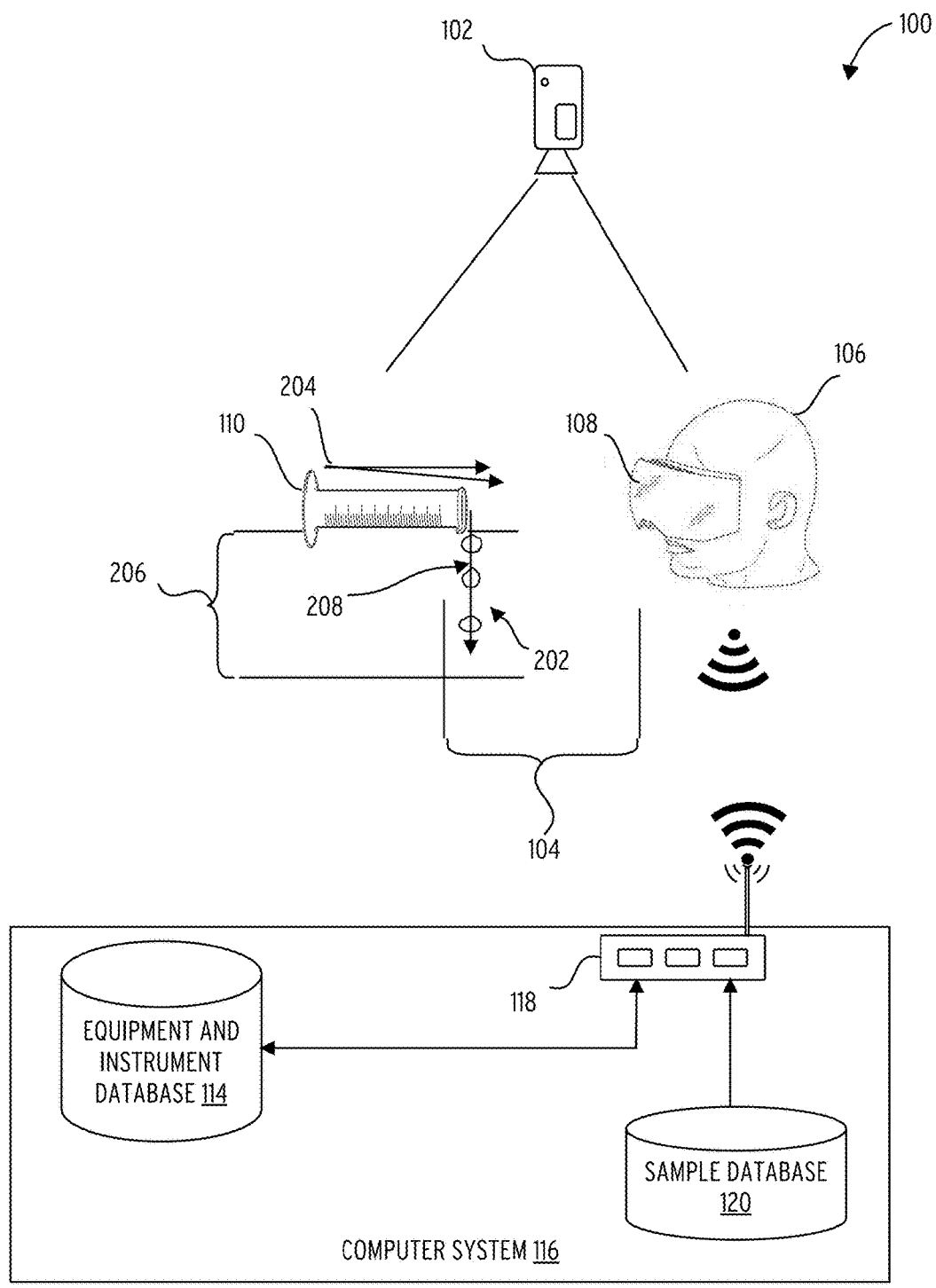
FIG. 2 illustrates another aspect of the augmented reality measurement system 100 in accordance with one embodiment.

The container 110 is imaged from at least two perspectives, one from the augmented reality headset 108 and one from the camera 102. Other cameras may be utilized to provide additional fields of view on the container 110. Referring to FIG. 2, the container 110 is then oriented such that droplets 202 emerge from it.

Liquid from the container 110 is poured at a constant rate slow enough to produce the droplets 202. This may entail feedback from the augmented reality headset 108 to the human operator 106 to modify the speed (faster or slower) that the droplets 202 are poured out, and may for example utilize a display on the augmented reality headset 108 of an angle 204 to orient the container 110 to produce the desired rate of pour, based on real-time analysis of whether or not the droplet profile necessary for viscosity and/or density analysis is being formed.

The type of the container 110 may be determined by way of computerized object recognition using the camera 102 and/or augmented reality headset 108, or because the human operator 106 designates the type of the container 110 using voice recognition. Dimensions of the container 110 are then either calculated from the image of the container 110 (e.g., as compared to a size in the image of a reference object in the field of view, the reference object at a known distance from the camera 102 or augmented reality headset 108). Dimensions of the container 110 may also be extracted from an equipment and instrument database 114 that associates object types with their dimensions. The augmented reality headset 108 may communicate wirelessly with a computer system 116 via a wireless gateway 118 to read and write equipment data to the equipment and instrument database 114 and from a sample database 120 comprising an association of material properties with known compositions.

The sample distance 104 may be determined by calibration to a known distance (e.g., the length of an arm of the human operator 106) and/or by utilizing a depth sensor system of the augmented reality headset 108. The camera 102 may be used together with the augmented reality headset 108 to triangulate the sample distance 104. The augmented reality headset 108 may also incorporate sonic depth sensors (e.g., LIDAR). Distance determination algorithms utilizing image analysis and/or sonic signals are known in the art.

For the measured angle 204, a size of each of the droplets 202 and a number of the droplets 202 falling per second through a defined vertical distance 206 are measured. For a defined axis of symmetry 208 around which the droplets 202 can be assumed to be symmetrical, a count of image pixels per droplet may provide a working analytical basis for estimating the size and volume of the droplets 202.

An aspect ratio of the droplets 202 (e.g., how round vs. teardrop shape they are) may also be determined from a pixel count and the axis of symmetry 208 for each droplet.

An estimate of the density and/or viscosity of the droplets 202 may be determined by measuring the fall time for a volume, aspect ratio, and cross section (e.g., widest cross section) as each drop falls through the vertical distance 206. For many lab experiments, the vertical distance 206 may vary between 0.2 meter and one meter of air at standard Earth gravity acceleration and atmospheric pressure. The determined density for many droplets 202 may then be averaged to determine an approximate density of the liquid in the container 110.

The density and/or viscosity of the droplets 202, and/or their aspect ratio and cross section may also be utilized to quality the composition of the liquid in the container 110, by referencing the sample database 120 for known compositions having those properties. Other features recorded by the camera 102 and/or the augmented reality headset 108 that may be utilized for the qualitative analysis of the composition include it's color and light permeability (opaqueness).

A volume of liquid in the container 110 may be determined by first determining a volume of the container 110 as previously described (e.g., identifying the type of the container 110 and looking up its volume in the equipment and instrument database 114, or via image analysis). The liquid boundaries 112 may then be identified using known techniques. One such technique is described in "Computer vision-based recognition of liquid surfaces and phase boundaries in transparent vessels, with emphasis on chemistry applications" by Sagi Eppel and Tal Kachman, Cornell University Library, 6 Nov. 2014.

The volume of liquid in the container 110 may then be estimated from the liquid boundaries 112 and using values interpolated from numbers read from the container 110, and/or values stored in the equipment and instrument database 114, or using volumetric equations specific to the geometry of the container 110.

Figure 3:
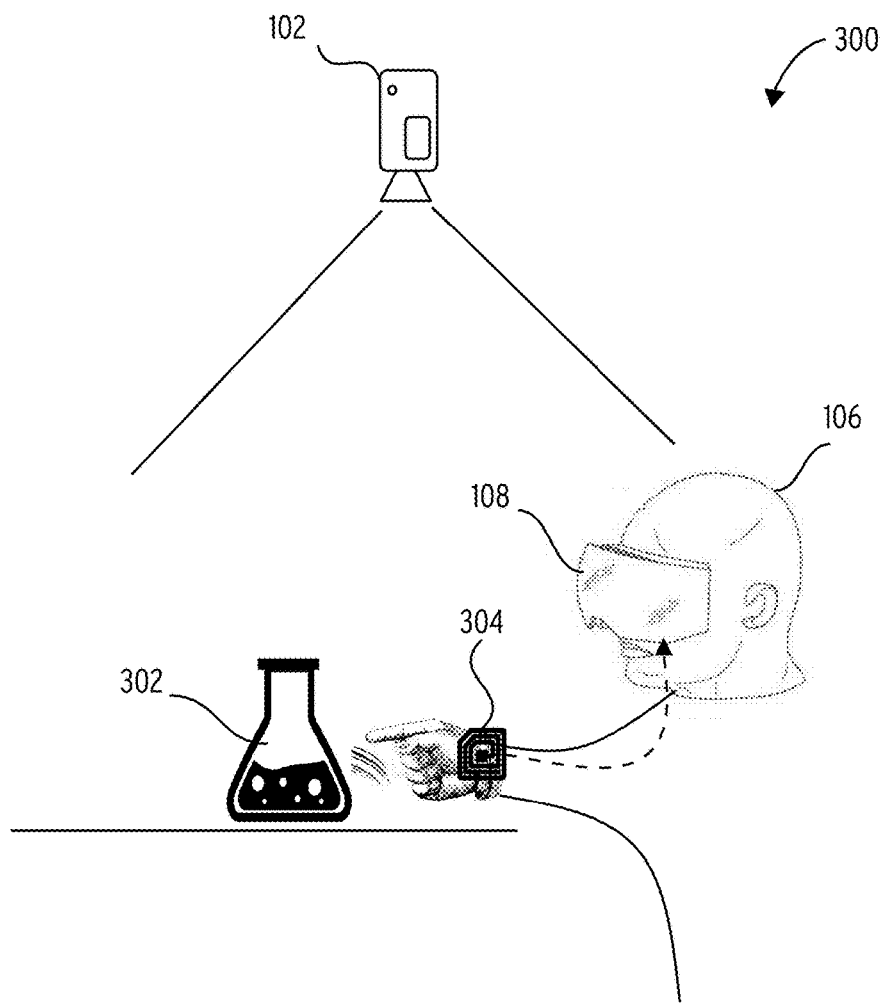
FIG. 3 illustrates an augmented reality measurement system 300 in accordance with one embodiment.

Referring to FIG. 3, an augmented reality measurement system 300 may be utilized to determine the composition, density, and mass of material from image analysis of a container 302 being hefted, poked, squeezed, jiggled, shaken, or otherwise physically perturbed.

The human operator 106 applies approximately calibrated forces to the container 302. Calibration and control of the applied forces may be facilitated by the augmented reality headset 108, which may incorporate feedback from a force feedback sensor 304 in a glove or other device.

The augmented reality headset 108 and/or camera 102 may capture and analyze images or video of the disturbance or change to material in the container 302 (e.g., movement, acceleration, deformation), for example as disclosed by Güler et al. 2014 and Güler et al. 2015, below.

Güler, P., Bekiroglu, Y. Gratal, X. Pauwels, K. and Kragic, D. "What's in the container? Classifying object contents from vision and touch", 2014 IEEE/RSJ International Conference on Intelligent Robots and Systems (IROS 2014). DOI: 10.1109/IROS.2014.6943119

Güler, P., Pauwels, K. Pieropan, A., Kjellström H., and Kragic, D. (2015). "Estimating the deformability of elastic materials using optical flow and position-based dynamics", IEEE-RAS International Conference on Humanoid Robots, 2015. DOI: 10.1109/HUMANOIDS.2015.7363486

The augmented reality measurement system 300 may for example utilize lookup tables in the sample database 120 cross referenced to lookup tables in the equipment and instrument database 114 for records of experimentation (e.g., hefting, poking, squeezing, jiggling, and shaking) containers of known volume filled with substances of known composition, including information about composition, density and mass. The tables may comprise empirical results of actions on containers performed by a set of people who span a gamut of known genders and sizes, and levels of physical fitness (eg. 50 kilogram women, 90 kilogram men), or by calibration using objects of known properties by the specific human operator 106.

The augmented reality measurement system 300 may in some embodiments estimate masses and forces being exerted to cause quantified motion by reference to simulated force generated by human arms of known dimensions moving masses of known weight, using for example open source software and models such as OpenSim (for example the Arm26 Model, 2016).

Figure 4:
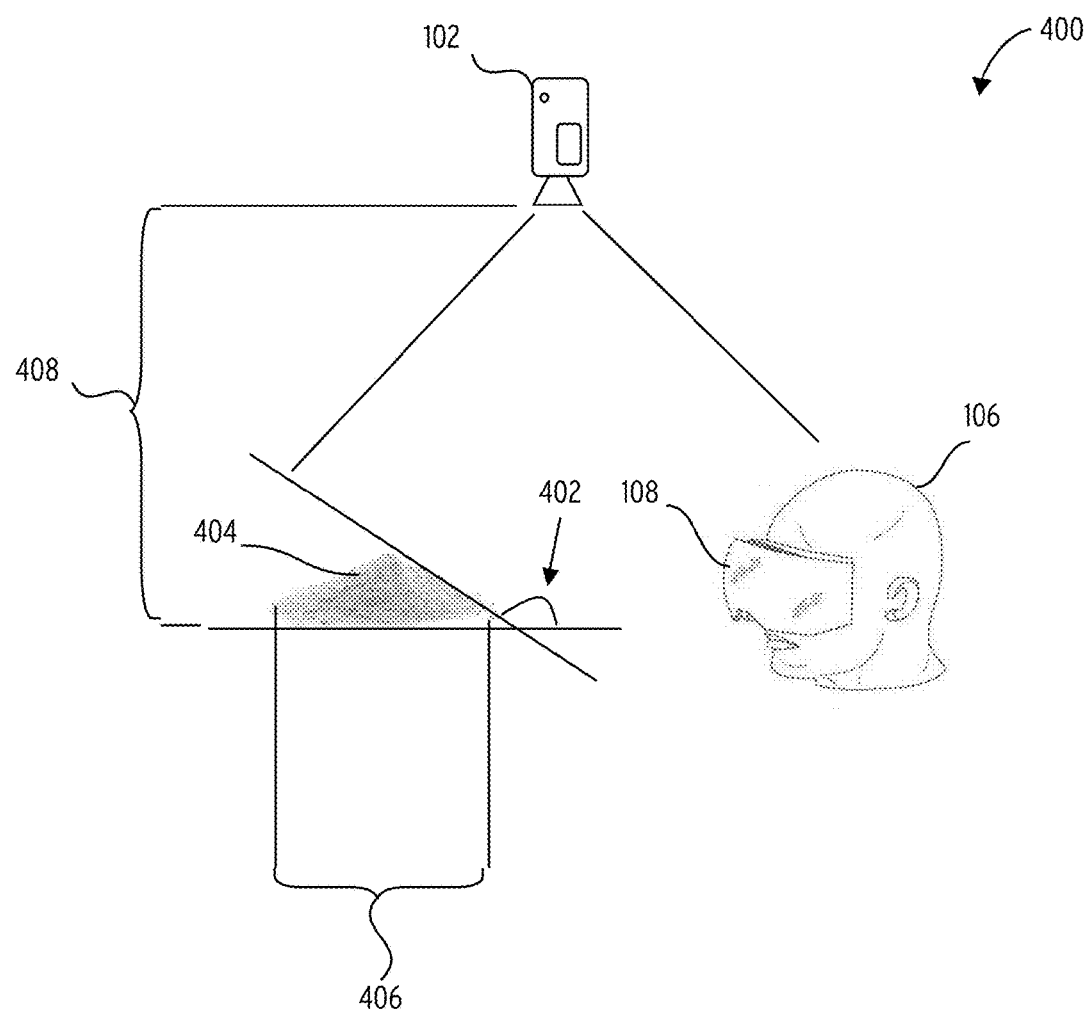
FIG. 4 illustrates an augmented reality measurement system 400 in accordance with one embodiment.

Referring to FIG. 4, an augmented reality measurement system 400 may be used to determine characteristics of a powdered or granulated sample 404. In one embodiment characteristics of the powdered or granulated sample 404 may be determined from an angle of repose 402 of the powdered or granulated sample 404 using inputs from the augmented reality headset 108 and one or more strategically positioned camera 102.

One type of characterization for the powdered or granulated sample 404 is the determination of amount of moisture or size of the grains in the powdered or granulated sample 404. This determination may be facilitated by a measure of the angle of repose 402 of the powdered or granulated sample 404.

One or more image from the augmented reality headset 108 and/or the camera 102 may be analyzed to calculate the angle of repose 402, for example as described in conjunction with FIG. 4 of "Assessment of angle of repose of granular plant material using computer image analysis", by J. Fraczek et al., Journal of Food Engineering 83 (2007) 17-22.

The angle of repose 402 may also be utilized to determine a volume of the powdered or granulated sample 404, according to a base radius or base diameter 406 of the powdered or granulated sample 404 calculated by scale analysis of an image of the powdered or granulated sample 404, and the sample vertical distance 408 from the camera 102 (or the augmented reality headset 108, or both).

To identify the portion of the image that includes the powdered or granulated sample 404, the human operator 106 may point manually to the pile, or the augmented reality headset 108 and/or camera 102 may identify the most pile-like object in the image through analysis or by matching against an image library of powdered or granulated samples, for example as stored by the sample database 120.

The human operator 106 may delineate the powdered or granulated sample 404 manually using hand gestures to trace the boundaries of the powdered or granulated sample 404 or to crop the image sufficiently that an algorithm such as described in Fraczek et al. is able to accurately operate.

If the powdered or granulated sample 404 has a shallow angle of repose 402, that is indicative that the powdered or granulated sample 404 has not gained a great deal of moisture from the environment. If the angle of repose 402 is steep, that is indicative that the powdered or granulated sample 404 has gained significant moisture content. The angle of repose 402 for a particular type of powdered or granulated sample 404, for example Argo cornstarch, may be recorded as a function of moisture in the sample database 120.

The particle size of a powdered or granulated sample 404 of known composition and moisture content may also be determined from the angle of repose. Larger particles will tend to have shallower angle of repose 402 for a fixed moisture composition. By first assuming a substantially dry (very low moisture content) for the powdered or granulated sample 404 of known composition, e.g., for flour), the particle diameter may be estimated by measuring the angle of repose 402 and comparing it to dry sample values for the powdered or granulated sample 404 in the sample database 120.

Figure 5:
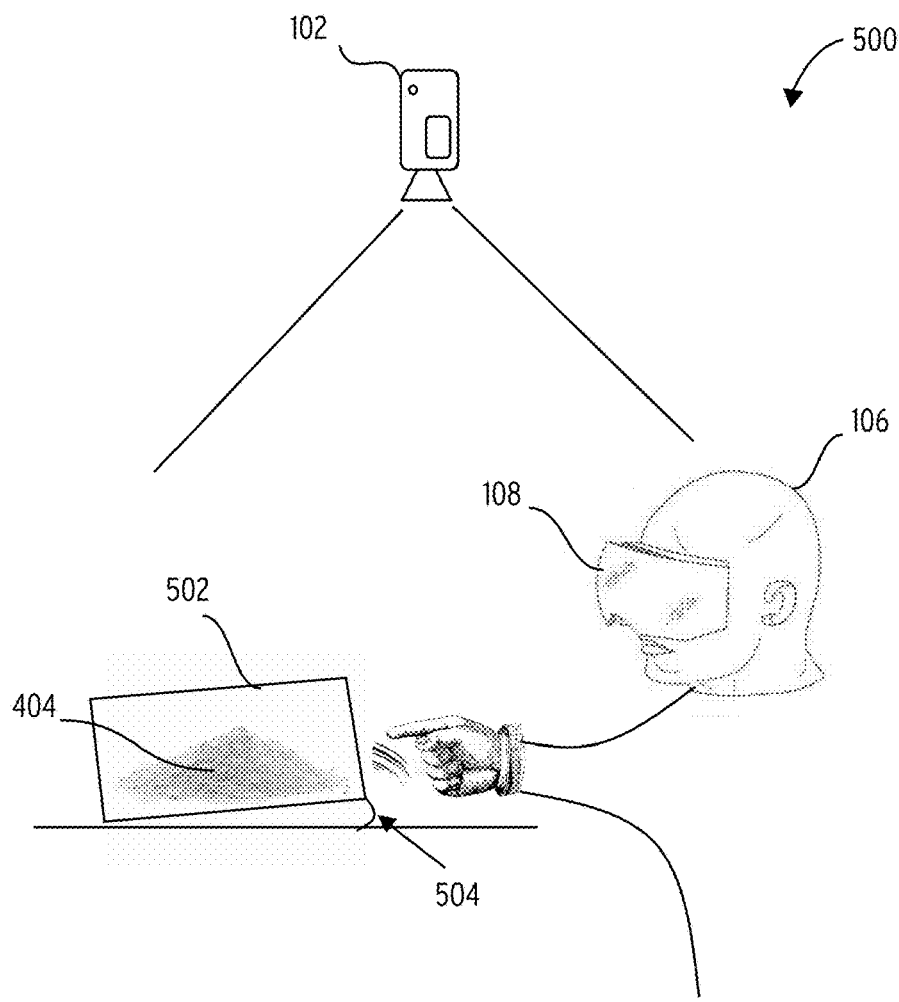
FIG. 5 illustrates an augmented reality measurement system 500 in accordance with one embodiment.
Figure 6:
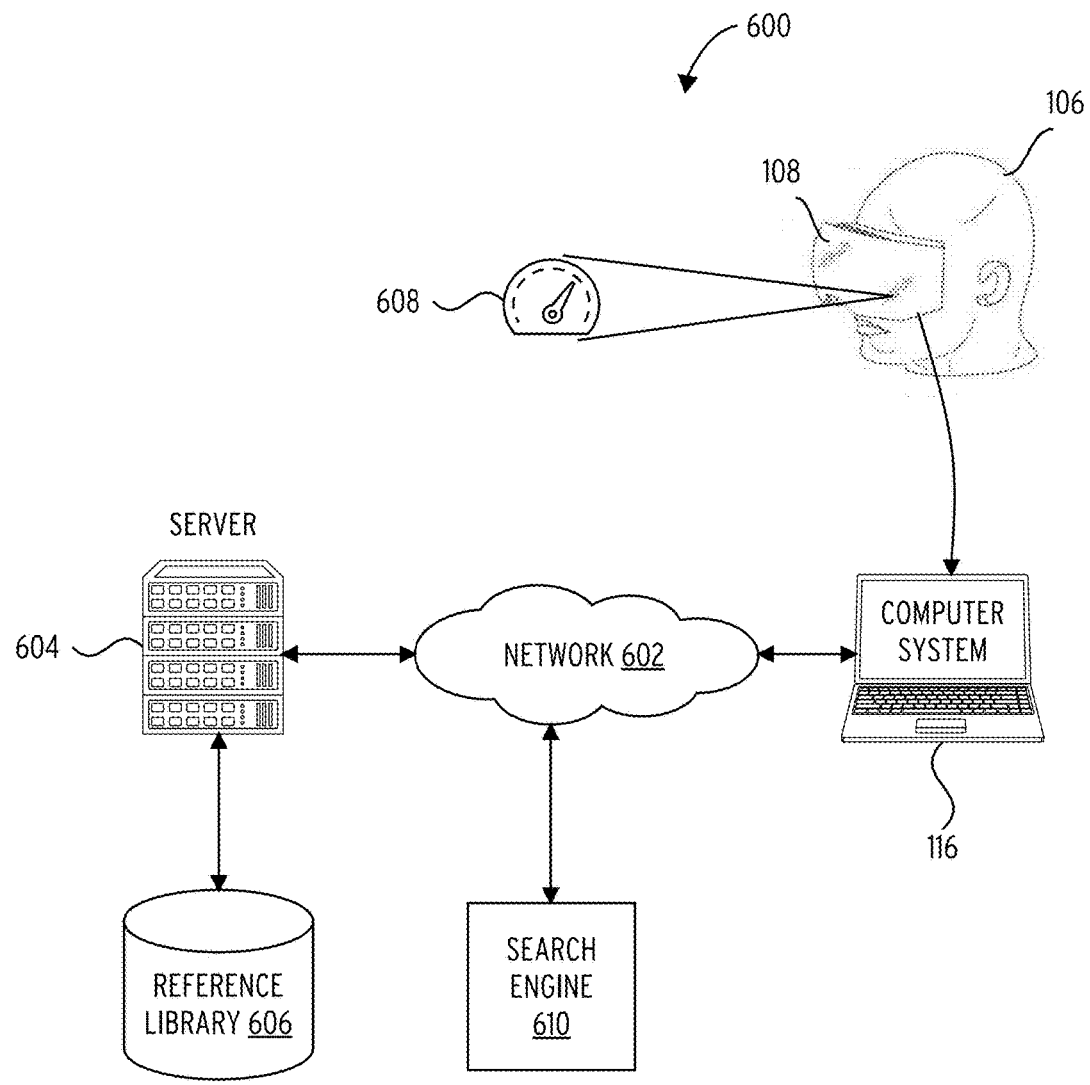
FIG. 6 illustrates the computer system 116 communicatively coupled to a network 602.

FIG. 5 illustrates another process to determine the amount of moisture or size of the grains in the powdered or granulated sample 404, referred to herein as a "tilting box" process. The powdered or granulated sample 404 is positioned within a container 502 with one or more transparent side to observe the behavior of the powdered or granulated sample 404 and the angle of repose 402 under mechanical change. The base diameter 406 of the material is leveled and parallel to the base of the container 502. The container 502 is slowly tilted at a rate, for example, of 0.30 per second. Tilting of the container 502 is stopped when the powdered or granulated sample 404 begins to slide in bulk, and the angle 504 of the tilt is measured using the augmented reality headset 108 and/or camera 102. The angle 504 may then be compared to angles associated with sample types having different material compositions, at different moisture levels, in the sample database 120 to determine a material and/or moisture composition of the powdered or granulated sample 404.

FIG. 2 illustrates an augmented reality measurement system 600 in which the computer system 116 is connected to one or more server 604 (e.g., a LAN server or web server) via a network 602. The server 604 provides access to a reference library 606 respository database. Contents of the reference library 606 may be indexed and searchable using a search engine 610.

In various embodiments, network 602 may include the Internet, a local area network ("LAN"), a wide area network ("WAN"), and/or other data network. In addition to traditional data-networking protocols, in some embodiments, data may be communicated according to protocols and/or standards including near field communication ("NFC"), Bluetooth, power-line communication ("PLC"), and the like. In some embodiments, network 602 may also include a voice network that conveys not only voice communications, but also non-voice data such as Short Message Service ("SMS") messages, as well as data communicated via various cellular data communication protocols, and the like.

In various embodiments, the computer system 116 may include desktop PCs, mobile phones, laptops, tablets, wearable computers, or other computing devices that are capable of connecting to network 602 and communicating with server 604, such as described herein.

In various embodiments, additional infrastructure (e.g., short message service centers, cell sites, routers, gateways, firewalls, and the like), as well as additional devices may be present. Further, in some embodiments, the functions described as being provided by some or all of server 604 and computer system 116 may be implemented via various combinations of physical and/or logical devices.

The reference library 606 may include digital materials (copyrighted or otherwise), for example digital reference material licensed to scientists, experimenters, teachers, and/or students from university libraries. The digital materials may include laboratory procedures generated and stored using embodiments of the augmented reality measurement systems described herein. By sensing and interpreting gestures, voice, or other user commands, an augmented reality measurement system may utilize the computer system 116 to record, retrieve, and display digital documents or lab procedures to and from the reference library 606, either directly or through links provided by the search engine 610. Retrieved materials or links thereto may be presented to the user of an augmented reality device on a visual display merged with objects, equipment, and/or materials in represented in the ocular field of view, or rendered to the user audibly, or saved in the user's electronic electronic notebook, or stored in personal (to the human operator 106) or institutional data repositories.

In some implementations of the system 600, the augmented reality headset 108 or the computer system 116 may include a usage meter 608 to track time of display and/or interaction between the human operator 106 and digital materials from the reference library 606. Usage information captured by the usage meter 608 may be communicated back to the reference library 606 for analysis.

The augmented reality measurement system detects measurable properties of materials in a user space and assists with identifying the type and state of the materials in question. The augmented reality measurement system may predict and report to the human operator 106 interactions between substances on a particle-level. Measuring and observing properties such as optical density, birefringence, schlieren, viscosity, and surface properties of a liquid, allows for inferences to be made about the that liquid, such as the number and size of cells and other particles in the liquid. Changes in optical density and above properties may also be indicative of changes in state in cells in culture (e.g., changes in size, shape, and partial lysis). When used to control peripheral machines, this becomes a particularly powerful technology which allows for a greater degree of precision in machine control of material handling by the human operator 106.

The outputs generated by the augmented reality measurement system may update an augmented reality or mixed-reality interface of the augmented reality headset 108 or other augmented reality device, enabling the human operator 106 to track material behavior predictions output by the system. The human operator 106 may adapt their actions or, if necessary, take manual control of the equipment and instruments in the ocular field of view if the predicted outcome is not congruent with the expected or desired outcome of the material handling process. The augmented reality measurement system may employ machine learning to improve its model and predictions of materials, equipment, and instruments, recording results and feedback from the human operator 106 and refining predictions for future interactions.

Figure 7:
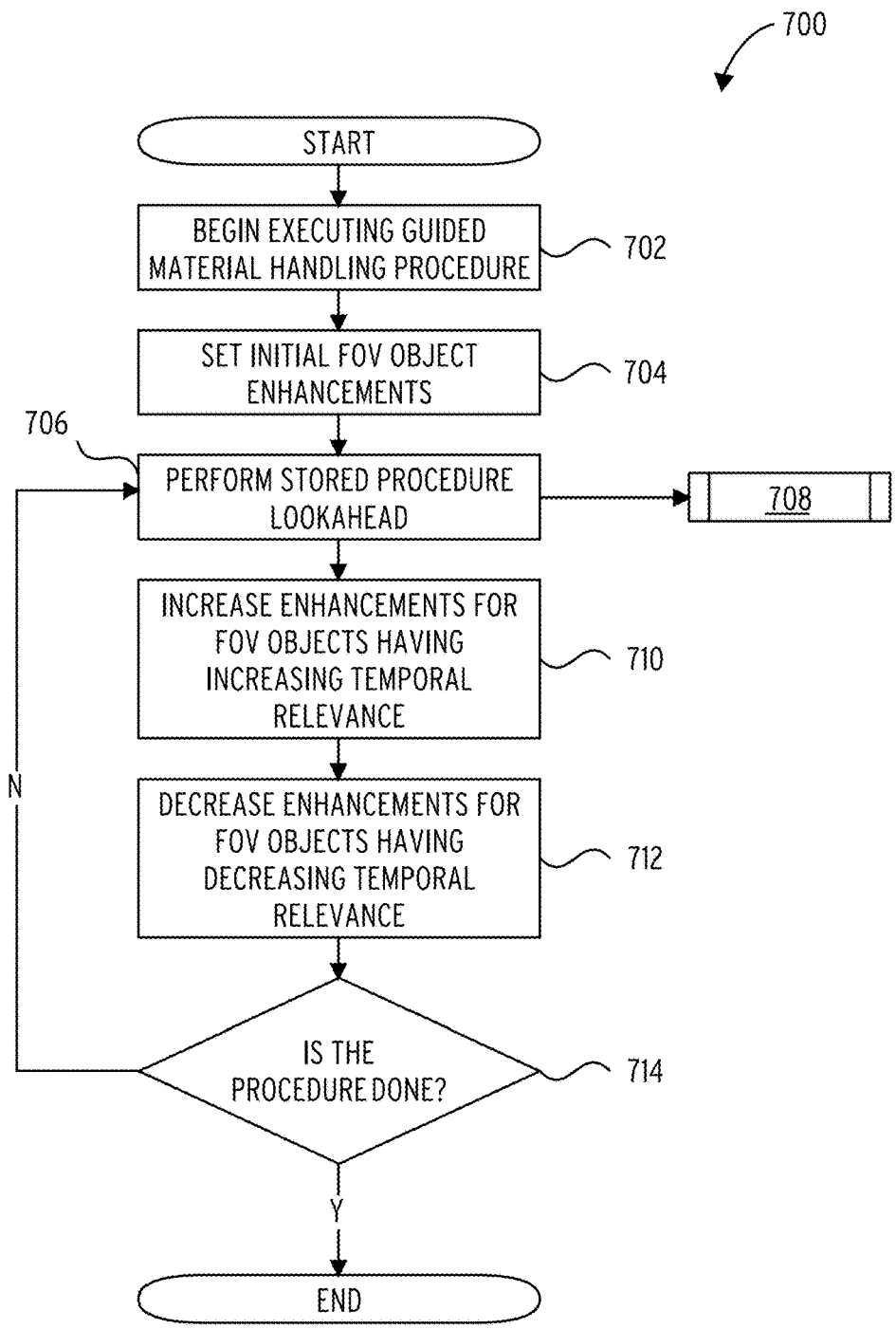
FIG. 7 illustrates an augmented reality process 700 in accordance with one embodiment.

Referring to FIG. 7, an augmented reality process 700 for assisting a human operator 106 with execution of stored material handling procedures may be carried out as follows:
begin executing guided material handling procedure 702;
set initial FOV object enhancements 704;
perform stored procedure lookahead 706; a recorded and stored description of a material handling procedure from a memory of the augmented reality headset 108 or the computer system 116, or an external system (e.g., reference library 606), may be analyzed for interactions with equipment or instruments in the user space that are more imminently relevant;
increase enhancements for FOV objects having increasing temporal relevance 710; this may include enhancing or adding an augmented reality outline of the more relevant objects, warming (changing toward a higher thermal temperature color, such as red or yellow or white) their overlayed or represented augmented reality color, or other visual enhancement techniques known in the art;
decrease enhancements for FOV objects having decreasing temporal relevance 712; this may include de-enhancing or removing an augmented reality outline of the more relevant objects, cooling (changing toward a lower thermal temperature color, such as red or yellow or white) their overlayed or represented augmented reality color, or other visual de-enhancement techniques known in the art;
is the procedure done? 714; if yes, the process 700 concludes; otherwise, it loops back to perform stored procedure lookahead 706 again.

The warming and cooling of objects in the graphical overlay may be proportional to their distance (in number of actions, or in time, or in probability of being interacted with given the current position in the documented action set) from a current position in the documented action set being facilitated by the augmented reality measurement system. In one embodiment, warming and cooling and gradual processes (e.g., gradient color changes) and not abrupt transitions in the representation of the equipment and instruments corresponding to upcoming actions in the documented action set in the graphical overlay.

The augmented reality process 700 continually monitors a stored procedure that is actively being carried out by the human operator 106, identifies a current point in the stored procedure at which the human operator 106 is operating, and looks ahead in the stored procedure for upcoming events involving interactions with equipment or instruments in the user space, and applies gradual augmented reality enhancements to the appearance of more temporally relevant (more relevant to upcoming actions in the procedure) objects. The enhancements are visually proportional to the imminence of the object's use in the stored procedure.

Figure 8:
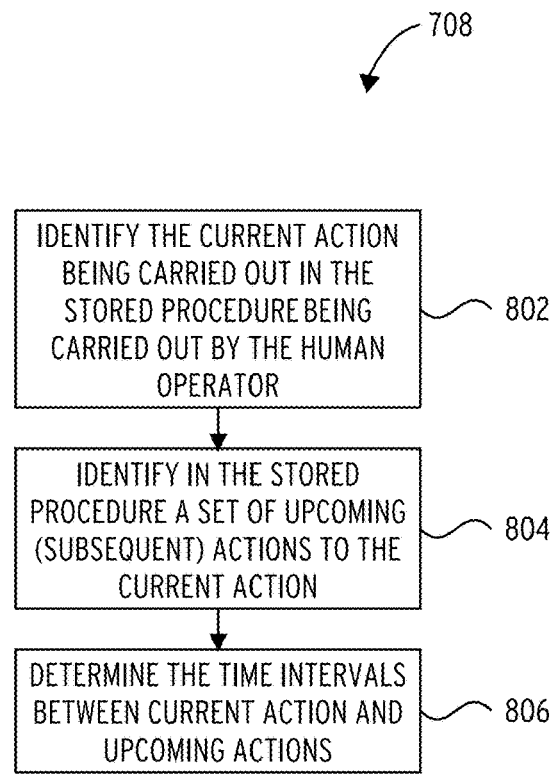
FIG. 8 illustrates a subroutine block 708 in accordance with one embodiment.

Referring to FIG. 8, a subroutine block 708 to perform stored procedure lookahead 706 may be carried out as follows:
identify the current action being carried out in the stored procedure being carried out by the human operator 802;
identify in the stored procedure a set of upcoming (subsequent) actions to the current action 804; and
determine the time intervals between current action and upcoming actions 806.

Enhancements (e.g., temperature color adjustments) to equipment and instruments in the ocular field of view may then be set based on the size of the time intervals (e.g., shorter intervals correspond to warmer color settings for the objects).

Figure 9:
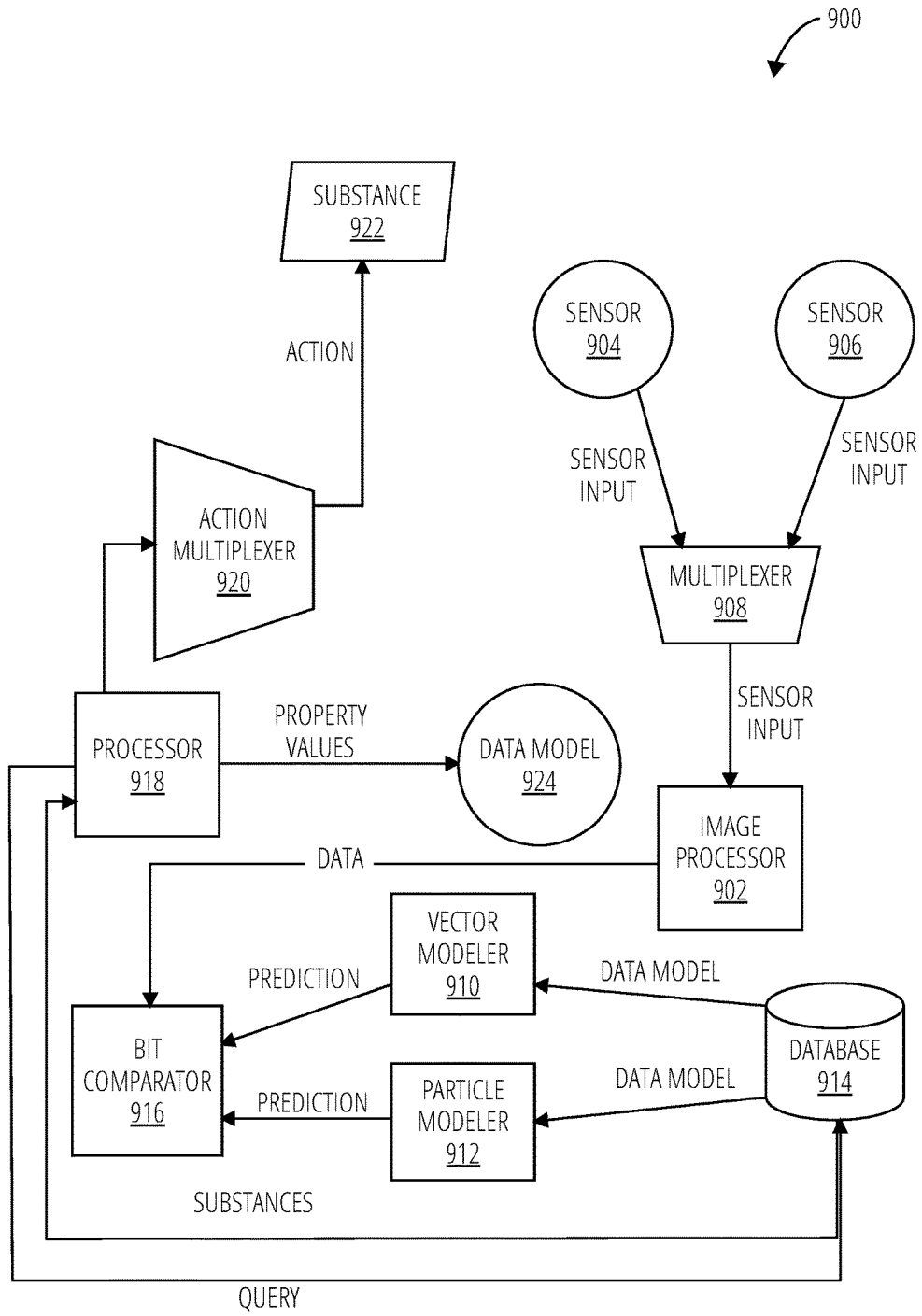
FIG. 9 illustrates an embodiment of a system 900 for interacting with substances.

Referring to FIG. 9, a system 900 for interacting with substances includes sensor 904, sensor 906, multiplexer 908, image processor 902, action multiplexer 920, data model 924, substance 922, processor 918, vector modeler 910, particle modeler 912, database 914, and bit comparator 916.

Figure 10:
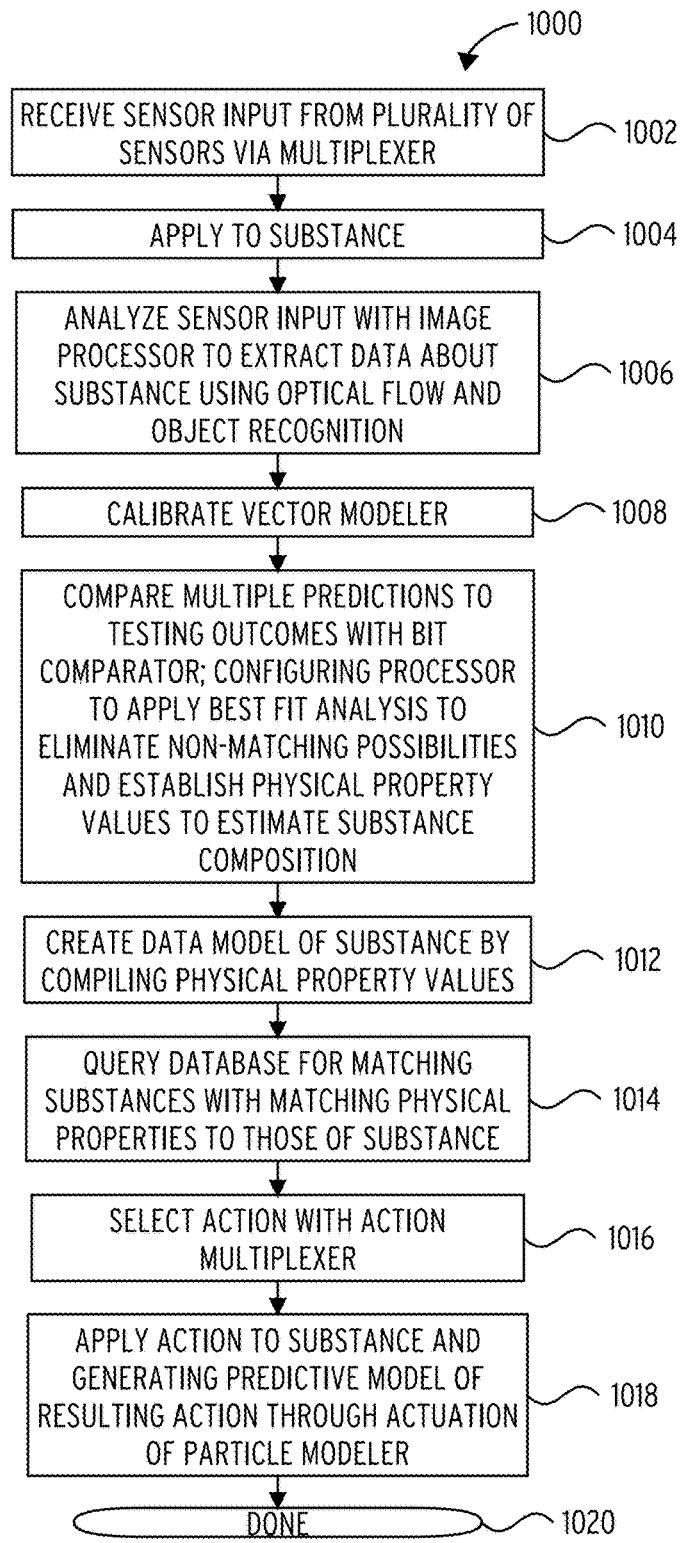
FIG. 10 illustrates an embodiment of a process 1000 for interacting with substances.

The system 900 may be operated in accordance with the processes described in FIG. 10.

Embodiments of the techniques described in conjunction with FIG. 1-FIG. 5 may be utilized in a process 1000 for interacting with substances. Referring to FIG. 10, in block 1002, the process 1000 receives sensor input from a plurality of sensors via a multiplexer. In block 1004, the process 1000 associates the inputs with a substance.

In block 1006, the process 1000 analyzes the sensor input with an image processor to extract data about the substance using optical flow and object recognition and in block 1008 calibrates a vector modeler.

In block 1010, the process 1000 compares the multiple predictions to testing outcomes with a bit comparator, configures a processor to apply a best fit analysis to eliminate non-matching possibilities, and establishes physical property values to estimate substance composition.

In block 1012, the process 1000 creates a data model of the substance by compiling the physical property values. In block 1014, process 1000 queries a database for matching substances with matching physical properties to those of the substance.

In block 1016, process 1000 selects an action to perform on the substance with an action multiplexer. In block 1018, the action is applied to the substance to generate a predictive model of a resulting action through actuation of the particle modeler. In done block 1020, the process 1000 ends.

By predicting the interactions of substances, the process 1000 allows for the efficient control of peripheral devices and machines. By analyzing substances and interactions, the process 1000 provides predictive and real-time feedback about the substances and the actions performed for purposes of recording and repeating material handling outcomes.

Thus in some embodiments, an augmented reality assisted method of identifying interactions of substances involves receiving sensor input from a group of sensors via a multiplexer, applying a substance analysis to one or more substances in an ocular field of view, selecting an action with an action multiplexer, applying the action to the substance(s) and generating a predictive model of an interaction result through actuation of a particle modeler.

The sensors used to gather information about the substances and the environment may include a user interface that may be operable by a human operator 106 to input observational data directly into an augmented reality measurement system. Inputs may include verbal, typed, or handwritten written descriptions about such things as the nature, composition, or state of a substance. The user interface and sensors may include a microphone and speech recognition logic to process narrative input from the user into observational data. The sensors may further include one or more of a camera, mass spectrometer, thermal sensor, and pressure sensor.

The augmented reality measurement system may query data sources such as equipment and instrument database 114 and sample database 120, search engines, or a reference library 606 that includes digital materials related to physical chemistry, chemistry, microbiology, physics, material handling for a particular task (e.g., cooking), mathematics, and/or previously recorded procedural logs. In some case the sensors may be operated in conjunction with optical character recognition (OCR) logic to process written notes of the human operator 106 into observational data.

The sensor input may be applied to an image processor to extract data about one or more substances using optical flow and object recognition. Predicting physical properties of the substance may be accomplished by calibrating a vector modeler and a particle modeler to generate multiple predictions about particle movement within the substance. These predictions may be based on applied stored data models for the substance physical properties. Predictions may include substance transformations and state changes, for example predictions based on the passage of time and actions performed with or to the substance(s).

multiple predictions from the system may be compared to stored epirical outcomes with a bit comparator, and a processor may be configured to apply a best fit analysis to eliminate non-matching possibilities and establish physical property values to estimate substance composition. A data model of the substance may be generated by compiling the predicted physical property values, and/or correlating the predicted properties with stored properties of known substances.

The substance analysis and the action may be applied to a group of substances and the particle modeler generates a predictive model. Generating the predictive model may include determining velocity and acceleration vectors for the substance.

Figure 11:
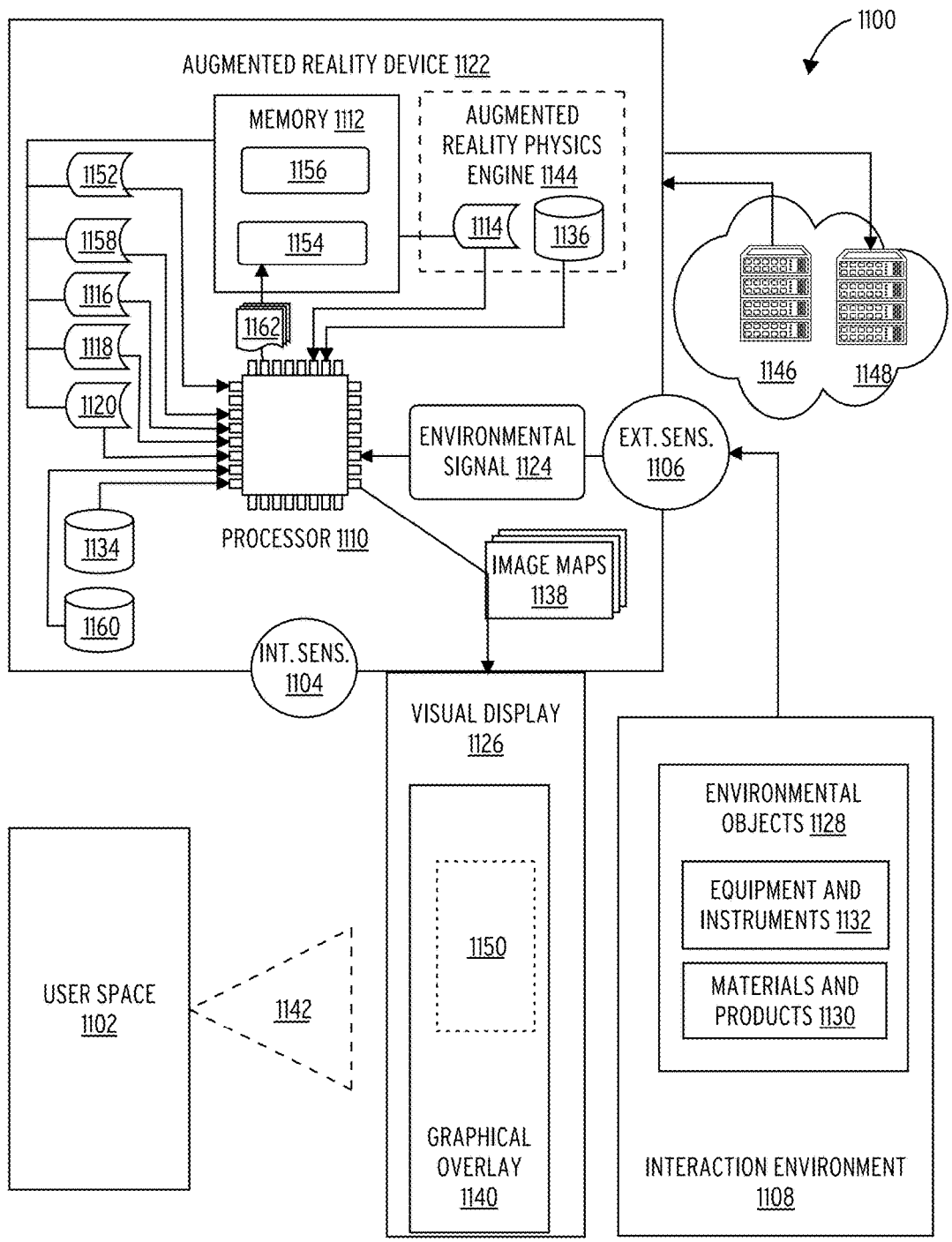
FIG. 11 illustrates an aspect of the subject matter in accordance with one embodiment.

FIG. 11 illustrates an embodiment of a system 1100 for guiding and documenting procedural actions of an action set through an augmented reality device. The system 1100 comprises a user space 1102, an interaction environment 1108, an augmented reality device 1122, a networked repository 1146, and a distribution server 1148.

The augmented reality device 1122 comprises augmented reality device 1122, image processing logic 1116, action set documentation logic 1152, behavior identification logic 1158, action set database 1160, an equipment and instrument database 1134, object targeting logic 1118, overlay synchronization logic 1120, an augmented reality physics engine 1144, a processor 1110, a plurality of internal transducers 1104, a plurality of external transducers 1106, a visual display 1126, and a communications link to the networked repository 1146 and the distribution server 1148.

The plurality of internal transducers 1104 typically will include gaze tracking devices, depth (distance) measurement devices, one or more microphone, one or more speaker, and other sensors and transducers commonly known in the art.

The memory 1112 comprises a data set allocation of memory 1156 and an action log allocation of memory 1154. The action log allocation of memory 1154 comprises interaction entries 1162. The plurality of external transducers 1106 identifies an environmental signal 1124.

The processor 1110 generates series of sequential image maps 1138 from the environmental signal 1124. The augmented reality physics engine 1144 comprises an object recognition logic 1114 and access to a materials database 1136.

The visual display 1126 comprises an ocular field of view 1142 directed towards a graphical overlay 1140. The graphical overlay 1140 comprises a graphical identifier 1150.

The interaction environment 1108 comprises an environmental objects 1128. The environmental objects 1128 comprises an equipment and instruments 1132 and a materials and products 1130. The system 1100 may be operated in accordance with the process described in FIG. 12.

Figure 12:
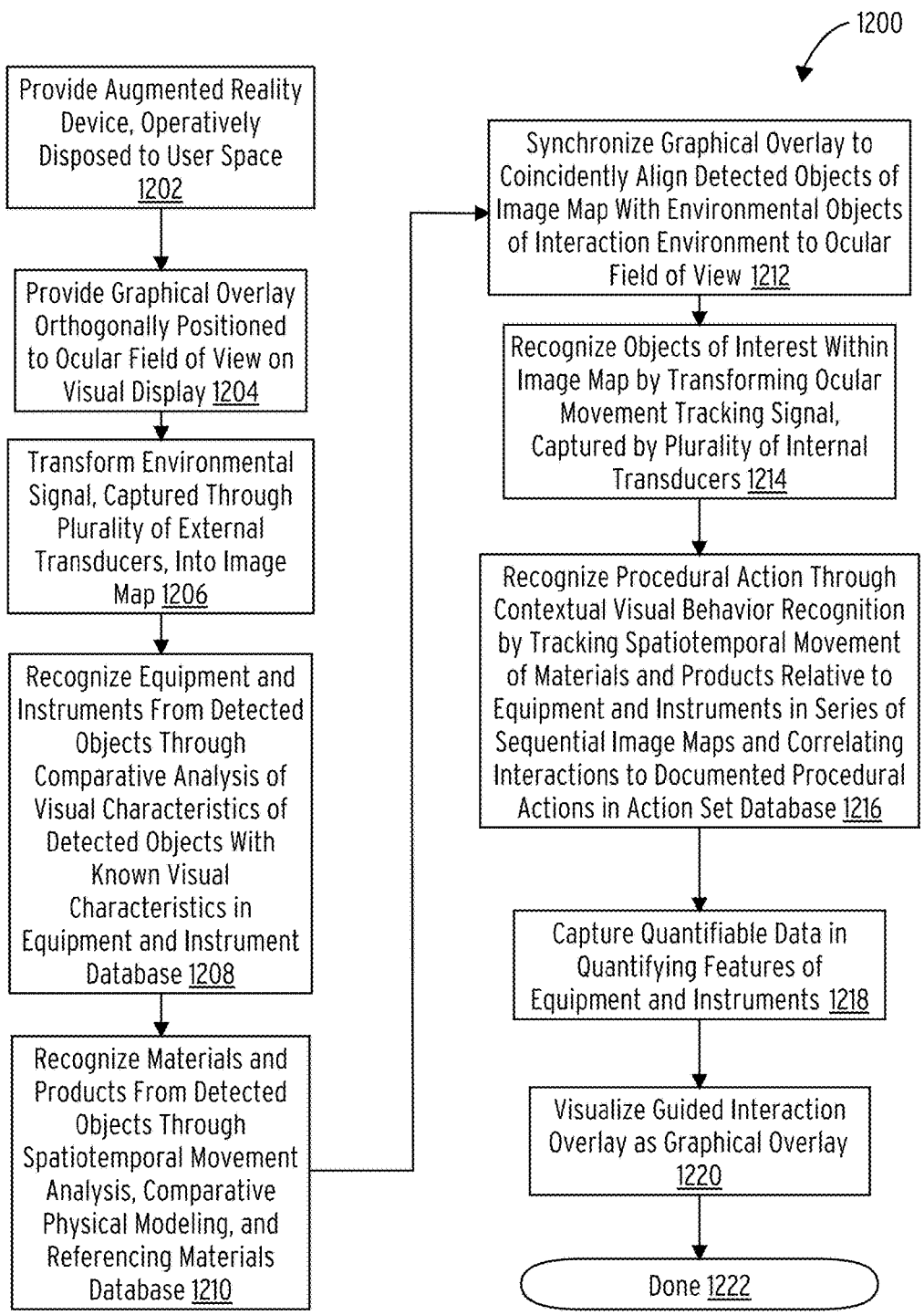
FIG. 12 illustrates an embodiment of a procedure 1200 for guiding and documenting procedural actions of an action set through an augmented reality device.

Referring to FIG. 12, in block 1202, the procedure 1200 provides the augmented reality device, operatively disposed to a user space. In block 1204, the procedure 1200 provides a graphical overlay orthogonally positioned to an ocular field of view on the visual display. In block 1206, the procedure 1200 transforms an environmental signal, captured through the plurality of external transducers, into an image map.

In block 1208, the procedure 1200 recognizes equipment and instruments from the detected objects through comparative analysis of visual characteristics of the detected objects with known visual characteristics in an equipment and instrument database. In block 1210, the procedure 1200 recognizes materials and products from the detected objects through spatiotemporal movement analysis, comparative physical modeling, and referencing a materials database.

In block 1212, the procedure 1200 synchronizes the graphical overlay to coincidently align the detected objects of the image map with the environmental objects of the interaction environment to the ocular field of view through operations of the processor controlled by overlay synchronization logic.

In block 1214, the procedure 1200 recognizes objects of interest within the image map by transforming an ocular movement tracking signal, captured by the plurality of internal transducers, into an ocular line of sight directed towards an environmental object in the interaction environment, with a corresponding detected object in the image map.

In block 1216, the procedure 1200 recognizes procedural action through contextual visual behavior recognition by tracking spatiotemporal movement of the materials and products relative to the equipment and instruments in the series of sequential image maps and correlating interactions to documented procedural actions in an action set database.

In block 1218, the procedure 1200 captures quantifiable data in quantifying features of the equipment and instruments through contextual feature analysis by correlating the procedural action.

In block 1220, the procedure 1200 visualizes a guided interaction overlay as the graphical overlay in response to an action set selection input of a documented action set from the action set database. In done block 1222, the procedure 1200 ends.

Figure 13:
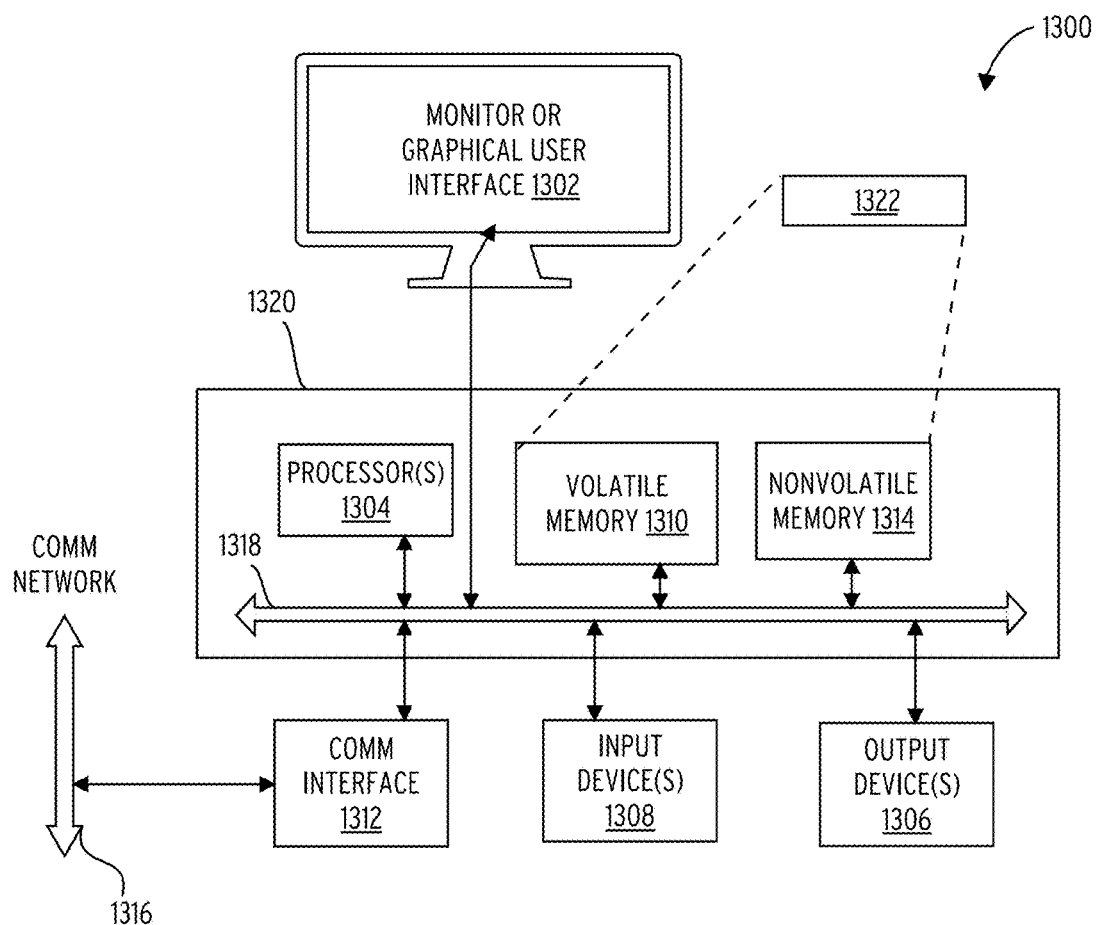
FIG. 13 is an example block diagram of a computing device 1300 that may incorporate embodiments of the present invention.

FIG. 13 is an example block diagram of a computing device 1300 that may incorporate embodiments of the present invention, e.g. computer system 116 (e.g., a desktop computer, server computer, smart phone, tablet) and/or augmented reality headset 108/augmented reality device 1122. FIG. 13 is merely illustrative of a machine to carry out aspects of the technical processes described herein, and does not limit the scope of the claims. One of ordinary skill in the art would recognize other variations, modifications, and alternatives.

In one embodiment, the computing device 1300 typically includes a monitor or graphical user interface 1302, a data processing system 1320, a communication network interface 1312, input device(s) 1308, output device(s) 1306, and the like.

As depicted in FIG. 13, the data processing system 1320 may include one or more processor(s) 1304 that communicate with a number of peripheral devices via a bus subsystem 1318. These peripheral devices may include input device(s) 1308, output device(s) 1306, communication network interface 1312, and a storage subsystem, such as a volatile memory 1310 and a nonvolatile memory 1314.

The volatile memory 1310 and/or the nonvolatile memory 1314 may store computer-executable instructions and thus forming logic 1322 that when applied to and executed by the processor(s) 1304 implement embodiments of the processes disclosed herein.

The input device(s) 1308 include devices and mechanisms for inputting information to the data processing system 1320. These may include a keyboard, a keypad, a touch screen incorporated into the monitor or graphical user interface 1302, audio input devices such as voice recognition systems, microphones, and other types of input devices. In various embodiments, the input device(s) 1308 may be embodied as a computer mouse, a trackball, a track pad, a joystick, wireless remote, drawing tablet, voice command system, eye tracking system, and the like. The input device(s) 1308 typically allow a user to select objects, icons, control areas, text and the like that appear on the monitor or graphical user interface 1302 via a command such as a click of a button or the like.

The output device(s) 1306 include devices and mechanisms for outputting information from the data processing system 1320. These may include speakers, printers, infrared LEDs, and so on as well understood in the art.

The communication network interface 1312 provides an interface to communication networks (e.g., communication network 1316) and devices external to the data processing system 1320. The communication network interface 1312 may serve as an interface for receiving data from and transmitting data to other systems. Embodiments of the communication network interface 1312 may include an Ethernet interface, a modem (telephone, satellite, cable, ISDN), (asynchronous) digital subscriber line (DSL), FIREWIRE®, USB, a wireless communication interface such as BLUETOOTH® or WI-FI®, a near field communication wireless interface, a cellular interface, and the like.

The communication network interface 1312 may be coupled to the communication network 1316 via an antenna, a cable, or the like. In some embodiments, the communication network interface 1312 may be physically integrated on a circuit board of the data processing system 1320, or in some cases may be implemented in software or firmware, such as "soft modems", or the like.

The computing device 1300 may include logic that enables communications over a network using protocols such as HTTP, TCP/IP, RTP/RTSP, IPX, UDP and the like.

The volatile memory 1310 and the nonvolatile memory 1314 are examples of tangible media configured to store computer readable data and instructions to implement various embodiments of the processes described herein. Other types of tangible media include removable memory (e.g., pluggable USB memory devices, mobile device SIM cards), optical storage media such as CD-ROMs, DVDs, semiconductor memories such as flash memories, non-transitory read-only-memories (ROMS), battery-backed volatile memories, networked storage devices, and the like. The volatile memory 1310 and the nonvolatile memory 1314 may be configured to store the basic programming and data constructs that provide the functionality of the disclosed processes and other embodiments thereof that fall within the scope of the present invention.

Software that implements embodiments of the present invention may be stored in the volatile memory 1310 and/or the nonvolatile memory 1314. Said software may be read from the volatile memory 1310 and/or nonvolatile memory 1314 and executed by the processor(s) 1304. The volatile memory 1310 and the nonvolatile memory 1314 may also provide a repository for storing data used by the software.

The volatile memory 1310 and the nonvolatile memory 1314 may include a number of memories including a main random access memory (RAM) for storage of instructions and data during program execution and a read only memory (ROM) in which read-only non-transitory instructions are stored. The volatile memory 1310 and the nonvolatile memory 1314 may include a file storage subsystem providing persistent (non-volatile) storage for program and data files. The volatile memory 1310 and the nonvolatile memory 1314 may include removable storage systems, such as removable flash memory.

The bus subsystem 1318 provides a mechanism for enabling the various components and subsystems of data processing system 1320 communicate with each other as intended. Although the communication network interface 1312 is depicted schematically as a single bus, some embodiments of the bus subsystem 1318 may utilize multiple distinct busses.

It will be readily apparent to one of ordinary skill in the art that the computing device 1300 may be a mobile device such as a smartphone, a desktop computer, a laptop computer, a rack-mounted computer system, a computer server, or a tablet computer device. As commonly known in the art, the computing device 1300 may be implemented as a collection of multiple networked computing devices. Further, the computing device 1300 will typically include operating system logic (not illustrated) the types and nature of which are well known in the art.

Those having skill in the art will appreciate that there are various logic implementations by which processes and/or systems described herein can be effected (e.g., hardware, software, or firmware), and that the preferred vehicle will vary with the context in which the processes are deployed. If an implementer determines that speed and accuracy are paramount, the implementer may opt for a hardware or firmware implementation; alternatively, if flexibility is paramount, the implementer may opt for a solely software implementation; or, yet again alternatively, the implementer may opt for some combination of hardware, software, or firmware. Hence, there are numerous possible implementations by which the processes described herein may be effected, none of which is inherently superior to the other in that any vehicle to be utilized is a choice dependent upon the context in which the implementation will be deployed and the specific concerns (e.g., speed, flexibility, or predictability) of the implementer, any of which may vary. Those skilled in the art will recognize that optical aspects of implementations may involve optically-oriented hardware, software, and or firmware.

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein. The techniques and procedures described herein may be implemented via logic distributed in one or more computing devices. The particular distribution and choice of logic will vary according to implementation.

The foregoing detailed description has set forth various embodiments of the devices or processes via the use of block diagrams, flowcharts, or examples. Insofar as such block diagrams, flowcharts, or examples contain one or more functions or operations, it will be understood as notorious by those within the art that each function or operation within such block diagrams, flowcharts, or examples can be implemented, individually or collectively, by a wide range of hardware, software, firmware, or virtually any combination thereof. Portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more processing devices (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

In a general sense, those skilled in the art will recognize that the various aspects described herein which can be implemented, individually or collectively, by a wide range of hardware, software, firmware, or any combination thereof can be viewed as being composed of various types of circuitry.

Those skilled in the art will recognize that it is common within the art to describe devices or processes in the fashion set forth herein, and thereafter use standard engineering practices to integrate such described devices or processes into larger systems. At least a portion of the devices or processes described herein can be integrated into a network processing system via a reasonable amount of experimentation. Various embodiments are described herein and presented by way of example and not limitation.

What is claimed is:

1. A method of identifying physical substances, comprising:
   receiving sensor input about a physical substance from a plurality of environment sensors via a multiplexer in an augmented reality environment;
   executing logic on a machine processor to:
      analyze the sensor input with an image processor comprising a camera to extract features of the physical substance using optical flow and object recognition;
      calibrating a vector modeler and a particle modeler to generate multiple predictions about particle movement within the physical substance based on existing data models for physical properties to generate multiple predictions of physical properties of the physical substance;
      comparing the multiple predictions of physical properties to testing outcomes for the physical substance;
      applying a best fit analysis to eliminate some of the multiple predictions of physical properties and to establish physical property values estimating a composition of the physical substance;
      generating a data model of the physical substance by compiling the physical property values; and
      querying a database for matching physical substances with matching physical properties of the physical properties of the physical substance;
   based on the matching physical substances, selecting via an augmented reality device with an action multiplexer an action from an action set of a stored procedure;
   indicating the selected action via the augmented reality device; and
   applying the action to the physical substance and generating a predictive model of an additional resulting action through actuation of the particle modeler and the vector modeler.

2. The method of claim 1, wherein the action is applied to a plurality of physical substances to generate the predictive model.

3. The method of claim 1, wherein extracting the features of the physical substance from the sensor input comprises applying analysis tools to the sensor input including one or more of image recognition, interpolation, and optical flow analysis.

4. The method of claim 1, wherein generating the multiple predictions about particle movement comprises:
   determining velocity and acceleration vectors for the physical substance.

5. The method of claim 1, wherein the plurality of sensors further comprises one or more of a camera, a mass spectrometer, a thermal sensor, and a pressure sensor.

6. The method of claim 1, wherein the plurality of sensors further comprises a user interface.

7. The method of claim 6, further comprising operating the user interface to display the predictive model of the resulting action.

* * * * *